United States Patent
Hoell, Jr. et al.

(10) Patent No.: US 12,000,388 B2
(45) Date of Patent: Jun. 4, 2024

(54) PERISTALTIC PUMP

(71) Applicant: NxStage Medical, Inc., Lawrence, MA (US)

(72) Inventors: Joseph A. Hoell, Jr., Dunbarton, NH (US); Alexander Muller, Goffstown, NH (US)

(73) Assignee: NxStage Medical, Inc., Lawrence, MA (US)

( * ) Notice: Subject to any disclaimer, the term of this patent is extended or adjusted under 35 U.S.C. 154(b) by 220 days.

(21) Appl. No.: 17/439,306

(22) PCT Filed: Mar. 13, 2020

(86) PCT No.: PCT/US2020/022778
§ 371 (c)(1),
(2) Date: Sep. 14, 2021

(87) PCT Pub. No.: WO2020/190778
PCT Pub. Date: Sep. 24, 2020

(65) Prior Publication Data
US 2022/0154711 A1    May 19, 2022

Related U.S. Application Data

(60) Provisional application No. 62/819,016, filed on Mar. 15, 2019.

(51) Int. Cl.
*F04B 43/12*    (2006.01)
(52) U.S. Cl.
CPC ............... *F04B 43/1284* (2013.01)

(58) Field of Classification Search
CPC .. F04B 43/1284; F04B 43/12; F04B 43/1253; F04B 43/1261; F04B 45/08
(Continued)

(56) References Cited

U.S. PATENT DOCUMENTS 328,472 A * 10/1885 Faller ............... F04B 43/1253
417/477.11
2,434,802 A * 1/1948 Jacobs ............... F04B 43/1253
417/412

(Continued)

FOREIGN PATENT DOCUMENTS

CN      104781556 A    7/2015
GB       1067529 A    5/1967

(Continued)

OTHER PUBLICATIONS

Extended European Search Report dated Aug. 8, 2022 for European Patent Application No. 20774179.4.
(Continued)

*Primary Examiner* — Bryan M Lettman
(74) *Attorney, Agent, or Firm* — Potomac Law Group, PLLC

(57) ABSTRACT

A peristaltic pump actuator includes a rotor element supporting rollers, the rotor element being configured to rotate about a rotor axis and the rollers each being configured to rotate about a roller axis that is parallel to the rotor axis. The rotor element and each of the rollers is constrained such that the rotor element and rollers are able to rotate only about their respective axes. A shoe having a displacement axis perpendicular to the rotor axis is forced against the rollers by an urging element without rotation in any axis. A tube may be placed between the shoe and the rollers.

15 Claims, 4 Drawing Sheets

(58) Field of Classification Search
USPC .......................................... 417/477.9, 477.11
See application file for complete search history.

(56) References Cited

U.S. PATENT DOCUMENTS

| | | | | |
|---|---|---|---|---|
| 3,791,777 | A * | 2/1974 | Papoff | F16L 21/005 |
| | | | | 417/475 |
| 3,918,854 | A * | 11/1975 | Catarious | A61M 5/14232 |
| | | | | 417/477.11 |
| 4,210,138 | A * | 7/1980 | Jess | A61M 5/16804 |
| | | | | 604/153 |
| 4,544,336 | A * | 10/1985 | Faeser | A61M 5/142 |
| | | | | 604/153 |
| 4,857,048 | A * | 8/1989 | Simons | A61M 5/14224 |
| | | | | 604/153 |
| 6,494,693 | B1 * | 12/2002 | Sunden | F04B 43/0072 |
| | | | | 417/474 |
| 2007/0212240 | A1 * | 9/2007 | Voyeux | F04B 43/1284 |
| | | | | 417/477.2 |
| 2012/0171063 | A1 * | 7/2012 | Al-Harbi | A61M 60/36 |
| | | | | 417/477.3 |
| 2015/0159643 | A1 * | 6/2015 | Koob | F04B 43/12 |
| | | | | 417/474 |
| 2016/0017880 | A1 * | 1/2016 | Maguire | F04B 43/1284 |
| | | | | 417/410.3 |
| 2017/0212240 | A1 | 7/2017 | Iwasaki | |
| 2018/0161486 | A1 * | 6/2018 | Repka | A61M 60/508 |

FOREIGN PATENT DOCUMENTS

| | | |
|---|---|---|
| JP | S50149902 U | 12/1975 |
| JP | H0475180 U | 3/1992 |
| JP | H0716059 A | 1/1995 |
| JP | 2008503687 A | 2/2008 |

OTHER PUBLICATIONS

International Search Report and Written Opinion dated Jun. 5, 2020 for International Patent Application No. PCT/US2020/022778.
Office Action (Notice of Reasons for Refusal) mailed Feb. 6, 2024 for Japanese Patent Application No. 2021-554739.
Office Action (First) issued Feb. 21, 2024 for Chinese Patent Application No. 202080021079.X.

* cited by examiner

PERISTALTIC PUMP

CROSS-REFERENCE TO RELATED APPLICATIONS

This Application is a U.S. national stage filing under 35 U.S.C. § 371 of International Application No. PCT/US2020/022778, filed Mar. 13, 2020, which claims priority to and the benefit of U.S. Provisional Patent Application No. 62/819,016 filed Mar. 15, 2019, each of which are hereby incorporated by reference in its their entireties.

BACKGROUND

Peristaltic pumps can pump fluid through tubing without exposing the fluid to contact with the tubing exterior or any of the pump components. This feature is relevant in medical and laboratory devices where maintaining the sterility of a fluid is often vital. An example of a fluid that is often pumped with a peristaltic pump is blood and other biological fluids. Such fluids are damaged by excessive pressure and lack of occlusion of the pump. For example, placing blood under high pressure in an extracorporeal tubing system may result in the blood cells being forced at high pressure through a narrow passage that is poorly occluded.

A peristaltic pump is a volumetric positive displacement pump that moves fluid through a tube by progressively compressing the fluid tube in one direction. A peristaltic pump typically comprises a housing having a semi-circular internal raceway formed on a shoe for receiving a fluid tube and a rotating member mounted in the center of the semi-circle formed by the raceway. The rotating member generally has roller elements that compress the fluid tube against the raceway.

For blood pumps, there is a spring that forces either the rollers toward the shoe or which forces the show toward the rollers. The force is often set to achieve full occlusion. For blood and other biological fluids this may be advantageous because it prevents the cells being damaged.

It will not be here attempted to set forth and indicate all of the various objects and advantages incident to the invention, but other objects and advantages will be referred to in or else will become apparent from that which follows.

SUMMARY

Objects and advantages of embodiments of the disclosed subject matter will become apparent from the following description when considered in conjunction with the accompanying drawings.

In embodiments, a peristaltic pump shoe has at least one rotational degree of freedom constrained. In embodiments, the shoe has at least two rotational degrees of freedom constrained. In embodiments, the shoe has three rotational and two displacement degrees of freedom constrained.

In embodiments, a peristaltic pump shoe is constrained by a linear bearing to sliding along the Z-axis. In embodiments, the linear bearing has a Polytetrafluoroethylene (PTFE) (e.g., Teflon™) liner. In embodiments, the linear bearing has two PTFE liners trapping a reservoir of lubricant between them.

In embodiments, the shoe engages an arc of the pump actuator that is less than 180 degrees. In embodiments, the shoe engages an arc of the pump actuator that is less than 150 degrees. In embodiments, the shoe engages an arc of the pump actuator that is less than 120 degrees.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

DETAILED DESCRIPTION

The invention will appear more clearly from the following detailed description when taken in connection with the accompanying drawings, showing by way of example a preferred embodiment of the inventive idea wherein like numerals refer to like parts throughout.

Figure 1C:
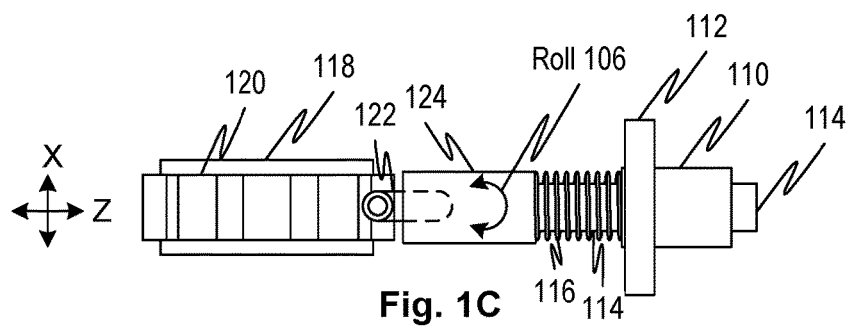
FIGS. 1A through 1C show a peristaltic pump from three orthogonal views, according to embodiments of the disclosed subject matter.
Figure 1A:
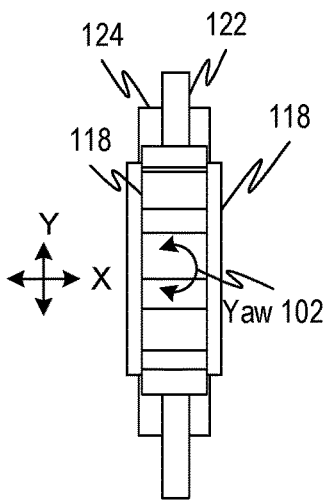
Figure 1B:
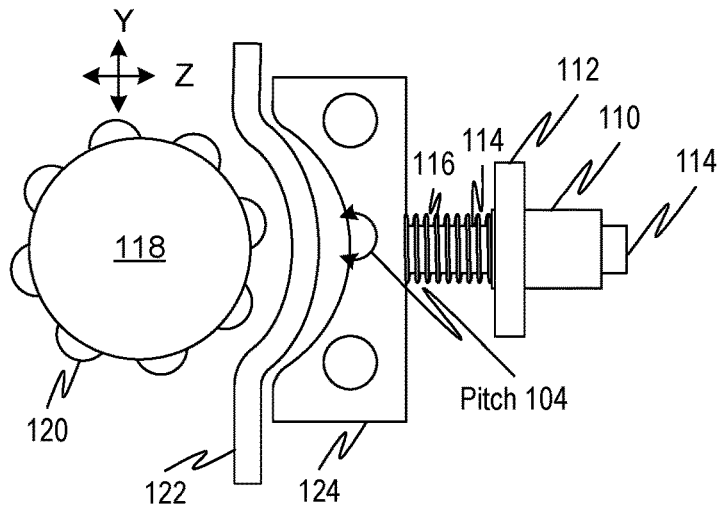

FIGS. 1A through 1C show a peristaltic pump from three orthogonal views, according to embodiments of the disclosed subject matter. FIG. 1A shows a top view looking at a pumping actuator 118 with the pumping tube segment 122 partially hidden. FIG. 1B shows a side view looking at a flat face of a pumping actuator 118. FIG. 1C shows the pump from an end view looking along the pumping tube segment 122. FIG. 1D shows the pump of FIGS. 1A through 1C with an actuator 118 engaging a pumping tube segment by way of rollers 120, according to embodiments of the disclosed subject matter. FIG. 1D shows the same view as FIG. 1B except that FIG. 1D shows the pumping tube clamped by the actuator between the pumping shoe and the actuator.

An actuator 118 has eight rollers 120 (only one indicated by the reference numeral in each figure to avoid clutter). Note that the actuator 118 can have any number of rollers and the example of eight rollers is not limiting of the disclosed subject matter. A pumping tube segment 122 is clamped between a pumping shoe 124 and the rollers 120. The pumping shoe 124 is constrained to move along a Z-axis by a linear bearing 110 that constrains the movement of a shaft 114 which is rigidly affixed to the pumping shoe 124. The linear bearing 110 constrains the rotational motion about the roll 106 and pitch 104 axes. A spring 116 urges the pumping shoe toward the pumping actuator. On one end, the spring 116 is held by bushing 112, which has a has a basin in which the end of the spring 116 sits. The basin prevents lateral movement of the spring 116. The spring is centrally-located about the shaft 114. In embodiments, the yaw motion can be constrained by means of a housing 130 (See FIG. 1E) within which the pumping shoe 124 slides.

Figure 1E:
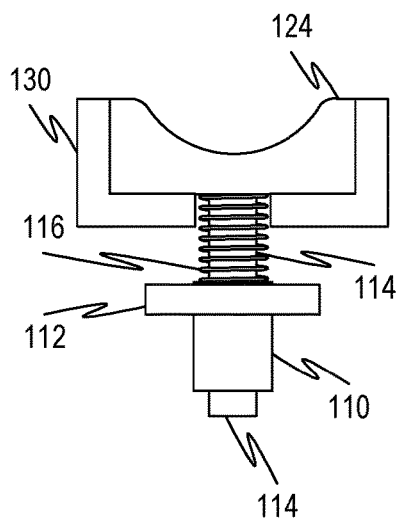
FIG. 1E shows a mechanism for constraining a pump shoe of the pump of FIGS. 1A through 1C, according to embodiments of the disclosed subject matter.
Figure 1D:
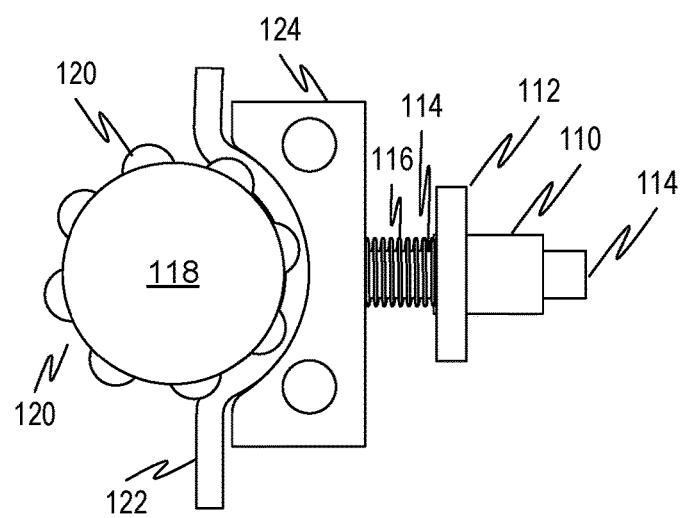
FIG. 1D shows the pump of FIGS. 1A through 1C with an actuator engaging a pumping tube segment, according to embodiments of the disclosed subject matter.
Figure 2A:
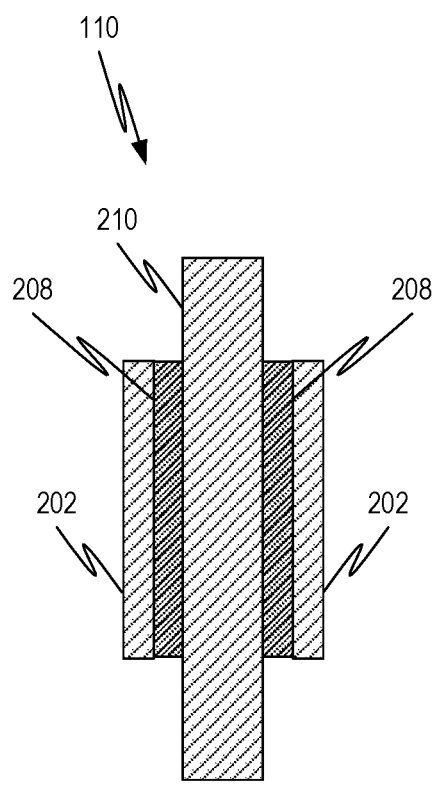
FIGS. 2A and 2B show linear bearings, according to embodiments of the disclosed subject matter.
Figure 2B:
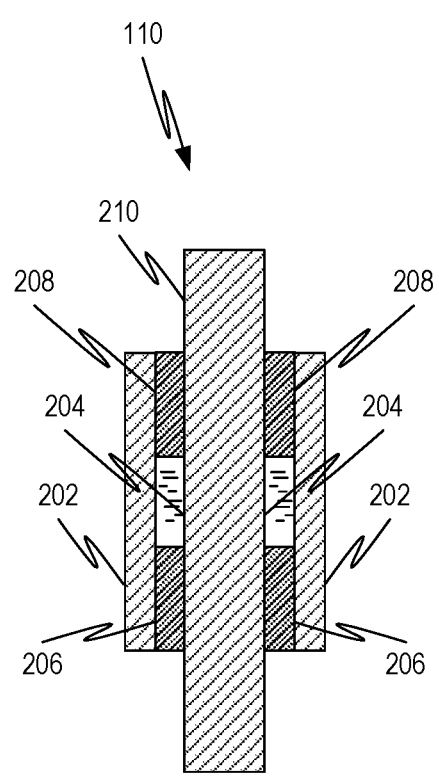

Note that the mechanism of FIG. 1E is capable of constraining against roll 106, pitch, 104 and yaw 102 motion and may be used as an alternative to the linear bearing 110 of FIGS. 1A through 1C. Thus, the linear bearing 110 and shaft 114 could be replaced by the housing 130 in embodiments. The linear bearing may be a metal cylindrical sleeve 202 with a PTFE liner 208 supporting a shaft 210 as shown in FIG. 2A. In an embodiment, shown in FIG. 2B, there are two PTFE liners 206 and 208 which enclose, in cooperation with the metal cylindrical sleeve 202 and the shaft 210 a reservoir of lubricant 204.

Figure 3:
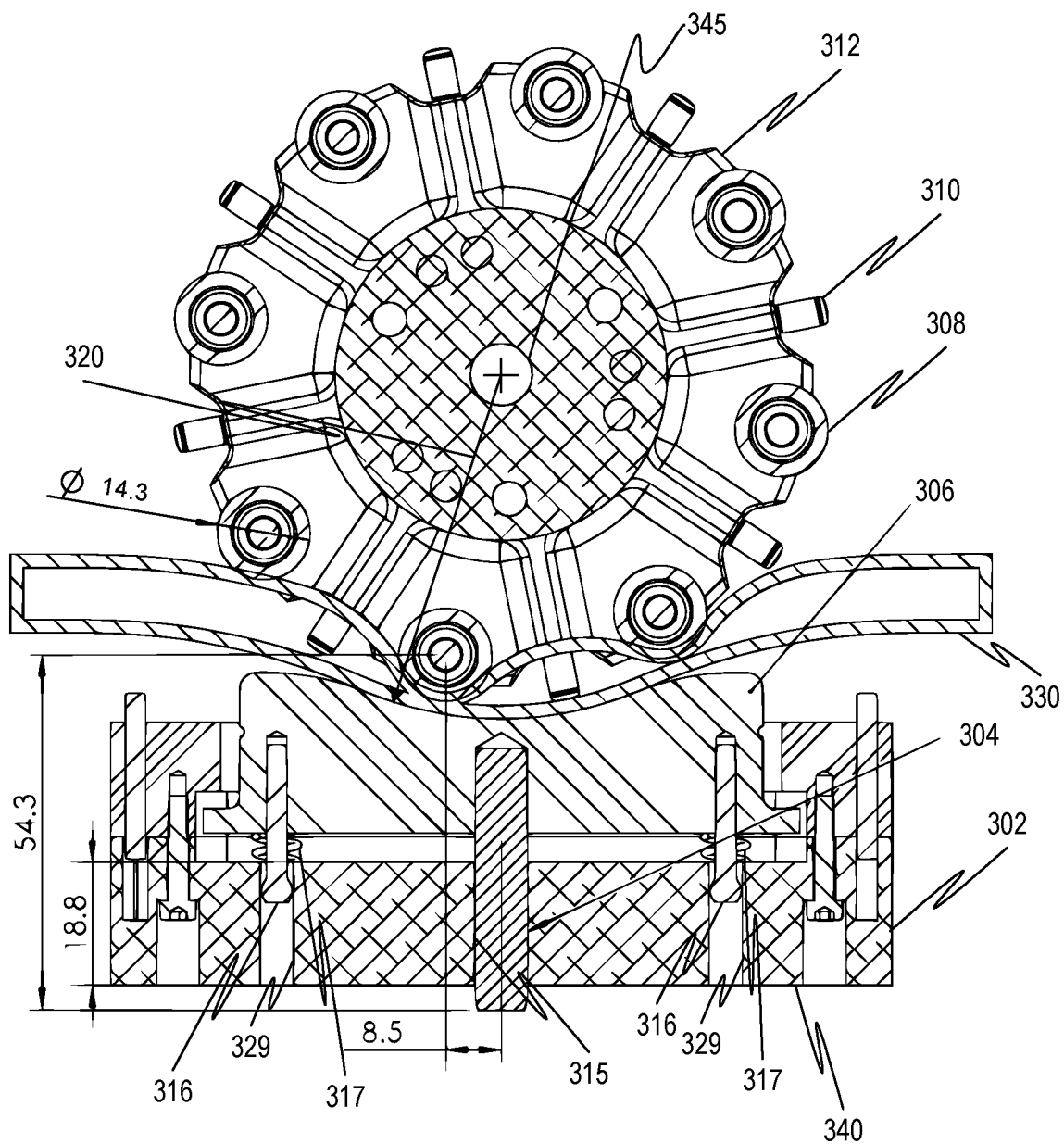
FIG. 3 shows a detailed embodiment of a peristaltic pump according to embodiments of the disclosed subject matter.

FIG. 3 shows a cross section (in a plane perpendicular to a rotor axle 345 of actuator 312) of a detailed embodiment of a peristaltic pump according to embodiments of the disclosed subject matter. An actuator 312 carries eight rollers 308 which rotate in a single direction and are otherwise constrained. The rollers 308 pinch a pumping tube segment 330 against a pump shoe 306. The pump shoe 306 has a curvature defined by radius 320 along a central region of the pump shoe 306. The pump shoe is urged by springs 317. The pump shoe is constrained from yaw rotation by pins 316. A linear bearing shaft 304, supported by a base 302, constrains the pump shoe against roll and pitch rotation by supporting Z-axis motion by sliding within a bore 315 in a base 340. Additional rollers 310 have axes of rotation along radii of the axis of the actuator 312 and serve to confine the pumping tube segment 330 against lateral movement with respect to the shoe 306. There may be a single roller 310 on each side of the pumping tube segment 330. These rollers 310 may extend on one or both sides of the pumping tube segment 330, thereby providing lateral support for the pumping tube segment 330. Guide pins 316 hold and position springs 317 to provide a force to urge the shoe 306 against the pumping tube segment 330 which is resisted by the rollers 308. The guide pins 316 slide within bores 329.

Figure 4A:
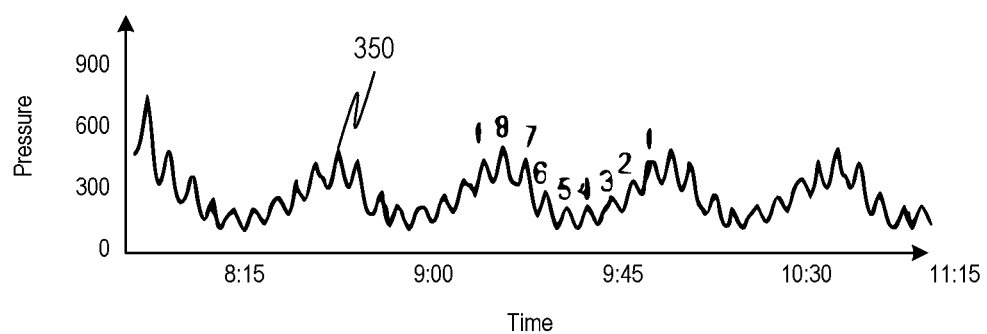
FIGS. 4A and 4B compare pressure fluctuations for a pump according to an embodiment with a prior art pump.
Figure 4B:
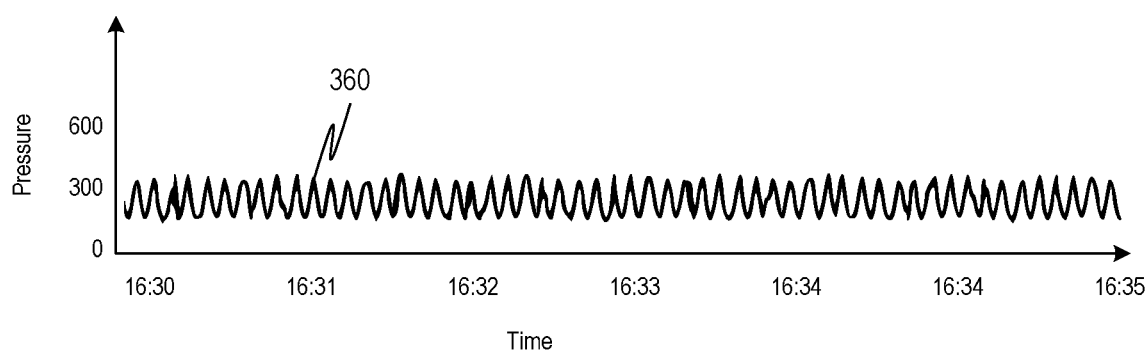

FIGS. 4A and 4B compare pressure fluctuations for a pump according to an embodiment with a prior art pump. The curve 350 of FIG. 4A represents a prior art pump. The curve is labeled with individual roller strikes to show that the lower frequency oscillation corresponds to the phase of the actuator. In the pump according to an embodiment, this low frequency oscillation is not present as shown by the curve 360 of FIG. 4B. The low frequency oscillation can be considered 1 revolution per minute (RPM) oscillation, as it repeats for every one revolution of the rotor (or actuator) that holds rollers. A consequence of this lack of a low frequency oscillation is that a minimum force required to obtain occlusion is reduced relative to the prior art pump.

In embodiments, the pump shoe is constrained against rolling rotation, only. Rotation in this mode can prevent full occlusion for a given force of compression of the pumping tube. Lack of full occlusion can cause damage to biological fluids such as blood. In the latter case, blood is forced backward through a small space causing hemolysis.

According to embodiments, the disclosed subject matter includes a peristaltic pump with an actuator with rollers that are held by the actuator such that they are free to rotate but otherwise fixed to the roller. A shoe is positioned to force a tube between the rollers and the shoe. The shoe is forced against the rollers and constrained against pivoting in at least one degree of freedom. The embodiments include variations in which the shoe is constrained against pivoting in all degrees of freedom. The embodiments include variations in which the shoe is constrained against all modes of displacement except toward and away from the actuator. The embodiments include variations in which the shoe is constrained against all modes of displacement except toward and away from the actuator. The embodiments include variations in which the shoe rides on a linear bearing. The embodiments include variations in which the shoe is constrained against yaw rotation by a sliding housing.

According to embodiments, the disclosed subject matter includes a method of operating a peristaltic pump that includes squeezing a tube between at least one actuator roller and a pump shoe by urging the pump shoe toward the at least one roller. The method includes constraining movement of the at least one roller in one rotating direction and constraining the pump shoe to a single displacement and no rotational directions.

The embodiments include variations in which the urging is effective to minimize a total force on the tube required for occlusion. The embodiments include variations in which the shoe is constrained against yaw rotation by a sliding housing. The embodiments include variations in which the shoe is constrained against yaw rotation by a sliding housing.

According to embodiments, the disclosed subject matter includes a peristaltic pump actuator. An actuator has rollers that are held by the actuator such that they are free to rotate but otherwise fixed to the roller. An urging mechanism is configured to urge the shoe toward the rollers. The shoe is forced against the rollers and constrained against pivoting in at least one degree of freedom. the shoe is constrained against yaw rotation by enclosing the shoe in a housing that permits only sliding motion in the Z-axis direction.

The embodiments include variations in which the urging mechanism includes a spring. The embodiments include variations in which the shoe is constrained against rotational motion, except along the Z-axis, by a linear bearing. The embodiments include variations in which the linear bearing includes a pair of PTFE liners and a lubricant. The embodiments include variations in which the linear bearing includes a pair of PTFE liners and a lubricant-soaked sponge. The embodiments include variations in which the shoe spans less than 150 degrees of arc. The embodiments include variations in which the shoe spans less than 120 degrees of arc. The embodiments include variations in which the pump generates pressure pulses with no 1 RPM components.

It will be observed that the arc of the actuator subtended by the shoe may be less than 180 degrees. In embodiments such as that of FIG. 4, the arc subtended may be less than 45 degrees. In other embodiments, the arc is less than 150, less than 120, less than 90, less than 60. In embodiments, because of the short arc, the initial state of the pumping tube may be straight.

It is, thus, apparent that there is provided, in accordance with the present disclosure, a peristaltic pump. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

The invention claimed is:
1. An actuator of a peristaltic pump, comprising:
 a rotor element supporting rollers, the rotor element being configured to rotate about a rotor axis and the rollers each being configured to rotate about a roller axis that is parallel to the rotor axis;
 the rotor element and each of the rollers being constrained such that the rotor element and rollers are able to rotate only about their respective axes; and
 a shoe having a displacement axis perpendicular to the rotor axis; and
 a linear bearing supporting the shoe, wherein the shoe is forced against the rollers by a spring without rotation in any axis, the shoe is constrained against all modes of displacement except toward and away from the rotor axis of the rotor element by the linear bearing, and the linear bearing includes an outer cylindrical sleeve which holds a pair of polytetrafluoroethylene (PTFE) sleeves spaced apart from each other, a supporting shaft passes through the pair of the PTFE sleeves, a cavity is defined by an outer surface of the supporting shaft, an inner surface of the outer cylindrical sleeve, and edges of each of the pair of the PTFE sleeves, and the cavity is filled with a lubricant.

2. The actuator of claim 1, wherein the pump is a peristaltic pump.

3. The actuator of claim 1, wherein said shoe is further constrained against yaw rotation by a sliding housing.

4. The actuator of claim 1, further comprising:

guard elements positioned along the rotor element between the rollers.

5. The actuator of claim 4, wherein the guard elements are second rollers, each of the second rollers having an axis extending radially away from the rotor axis and perpendicular to the rotor axis.

6. The actuator of claim 5, wherein each of the second rollers has a width measured along its axis, and the second rollers extend at least on one side of a pumping tube segment that is positioned between the rotor element and the shoe.

7. The actuator of claim 6, wherein the second rollers extend on both sides of the pumping tube segment.

8. The actuator of claim 1, wherein the shoe spans less than 150 degrees of arc.

9. The actuator of claim 1, wherein the peristaltic pump generates pressure pulses without 1 RPM components.

10. The actuator of claim 1, wherein the lubricant is soaked in a sponge that is disposed in the cavity.

11. A method of operating a peristaltic pump, comprising:

squeezing a tube between at least one actuator roller and a pump shoe by urging the pump shoe toward the at least one actuator roller; and constraining movement of the at least one actuator roller in one rotating direction and constraining the pump shoe to a single displacement and no rotational directions by a linear bearing that includes an outer cylindrical sleeve which holds a pair of Polytetrafluoroethylene (PTFE) sleeves spaced apart from each other, a supporting shaft passing through the pair of the PTFE sleeves, a cavity being defined by an outer surface of the supporting shaft, an inner surface of the outer cylindrical sleeve, and edges of each of the pair of the PTFE sleeves, and the cavity being filled with a lubricant.

12. The method of claim 11, wherein the urging is effective to minimize a total force on the tube required for occlusion.

13. The method of claim 12, wherein said pump shoe is constrained against yaw rotation by a sliding housing.

14. The method of claim 11, wherein said pump shoe is constrained against yaw rotation by a sliding housing.

15. The method of claim 11, wherein the lubricant is soaked in a sponge that is disposed in the cavity.

* * * * *